(12) United States Patent
Babikian et al.

(10) Patent No.: US 8,007,832 B2
(45) Date of Patent: Aug. 30, 2011

(54) CANCER TREATMENT

(76) Inventors: Yousef Haik Babikian, Amman-Jordan (JO); Walid Adib Taybeh, Amman-Jordan (JO)

( * ) Notice: Subject to any disclaimer, the term of this patent is extended or adjusted under 35 U.S.C. 154(b) by 1263 days.

(21) Appl. No.: 11/504,850

(22) Filed: Aug. 16, 2006

(65) Prior Publication Data

US 2007/0224291 A1    Sep. 27, 2007

(51) Int. Cl.
*A61K 33/28* (2006.01)
*A61K 33/30* (2006.01)
*A61K 31/194* (2006.01)

(52) U.S. Cl. ........ 424/643; 424/641; 424/642; 424/644; 424/645; 514/574

(58) Field of Classification Search .......... 424/641–645; 514/557, 574
See application file for complete search history.

(56) References Cited

PUBLICATIONS

Voskoglou-Nomikos, T. et al., "Clinical predictive value of the in vitro cell line, human xenograft, and mouse allograft preclinical cancer models," Clinical Cancer Research, vol. 9, pp. 4227-4239 (Sep. 2003).*
Zips, D. et al., "New anticancer agents: in vitro and in vivo evaluation," In Vivo, vol. 19, pp. 1-7 (2005).*
Toxicological Profile for Mercury. U.S. Department of Health and Human Services, Mar. 1999, pp. 154-157.*

* cited by examiner

*Primary Examiner* — Thomas H Tarcza
*Assistant Examiner* — Fred H Mull
(74) *Attorney, Agent, or Firm* — Abelman, Frayne & Schwab

(57) ABSTRACT

A composition and method for treating mammals suffering from malignant tumors which involves administering a composition including ammoniated mercury, zinc oxide and citric acid.

3 Claims, No Drawings

CANCER TREATMENT

FIELD OF THE INVENTION

The present invention relates generally to a composition for the treatment of malignant tumors and, more specifically, to its use in a method for the treatment of carcinomas and sarcomas.

BACKGROUND OF THE INVENTION

Breast cancer is a malignant abnormal cell growth in the breast. Cancer cells may spread to other areas of the body (called metastasis). Fibrocystic changes (e.g., formation of cysts, scar tissue) may cause benign (i.e., noncancerous) lumps in the breast.

In women, breast cancer is the second most common type of cancer and the second leading cause of cancer-related deaths. One in eight women in the United States will develop breast cancer during their lifetimes.

Approximately 200,000 women in the United States are diagnosed with breast cancer each year, and the disease causes about 40,000 deaths annually.

The incidence of breast cancer rises after age 40. The highest incidence (approximately 80% of invasive cases) occurs in women over age 50.

Most breast cancer develops in glandular tissue and is classified as adenocarcinoma. The earliest form of the disease, ductal carcinoma in situ (DCIS), develops solely in the milk ducts. The most common type of breast cancer, invasive ductal carcinoma (IDC), develops from DCIS, spreads through the duct walls, and invades the breast tissue.

Invasive lobular carcinoma originates in the milk glands and accounts for 10-15% of invasive breast cancers. Less common types of breast cancer include the following:
  Inflammatory (breast tissue is warm and appears red, and tends to spread quickly);
  Medullary carcinoma (originates in central breast tissue);
  Mucinous carcinoma (invasive; usually occurs in postmenopausal women);
  Paget's disease of the nipple (originates in the milk ducts and spreads to the skin of the nipples or areola);
  Phyllodes tumor (tumor with a leaf-like appearance that extends into the ducts; rarely metastasizes; and
  Tabular carcinoma (small tumor that is often undetectable by palpation).

While sarcomas (cancer of the connective tissue) and lymphomas (cancer of the lymph tissue) develop in the breasts, they are relatively rare occurrences.

Approximately 5% of breast cancer cases have a genetic link that results from an inherited mutation in genes identified as BRCA1 and BRCA2. Patients who inherit an altered BRCA1 or BRCA2 gene have an increased risk for developing premenopausal breast cancer and are more likely to have family members with the condition.

The cause of breast cancer is unknown.

The diagnosis of breast cancer is made through a process called triple assessment, which includes:
 1. clinical examination;
 2. imaging procedures e.g., mammogram, breast ultrasound, magnetic resonance imaging (MRI scan); and
 3. biopsy (surgical removal of tissue for microscopic examination) of a mass detected by physical examination or mammogram.

There are various options for the treatment of breast cancer. They include surgery, radiation, immunotherapy, hormonal, chemotherapy, and radiation or one or more of the foregoing options in combination.

Surgery combined with radiation and/or chemotherapy is the most common treatment for breast cancer. The type of surgical procedure recommended to the patient depends on the stage of the disease. Mastectomy is the most commonly performed procedure.

Radiation uses high-energy x-rays to destroy cancer cells. Treatment is delivered by a machine outside the body (called external radiation) or by radioactive "seeds" that are placed directly into the tumor (called brachytherapy). Breast cancer is usually treated using external radiation.

Radiation may be used to shrink the tumor before surgery (called neoadjuvant therapy) or may be used after surgery to destroy cancer cells that remain in the breast, chest wall, or underarm (called adjuvant therapy).

Radiation therapy is performed in a hospital or an outpatient center. Each treatment lasts a few minutes and treatment is usually given 5 days per week, for 6 weeks. Side effects include fatigue, reddening of the skin and swelling.

Several drugs have been developed to treat breast cancer that is responsive to estrogen. Selective estrogen-receptor modulators (SERMs; e.g., tamoxifen, raloxifene) inhibit the effects of estrogen on breast cancer cells.

Tamoxifen (Nolvodex®) is taken in pill form, usually for 5 years after breast cancer surgery to prevent recurrence. After 5 years, patients taking tamoxifen have an increased risk for early stage cancer of the lining of the uterus. The most common side effect of this medication is hot flashes. Other side effects include the following: depression, dizziness, hair loss, headache, and swelling. Studies are being conducted to determine if raloxifene (Evista®) can effectively reduce the risk for breast cancer. Side effects include hot flashes and leg cramps.

Fulvestrant (Faslodex®) destroys estrogen receptors in breast cancer cells. It is used to treat metastatic breast cancer in postmenopausal women who have been treated unsuccessfully with tamoxifen. This treatment is administered once a month by intramuscular injection. Side effects include nausea, hot flashes, and weight gain.

Goserelin (Zolodex®) is a synthetic form of luteinizing hormone-releasing hormone (LHRH) that is prescribed to treat metastatic breast cancer in premenopausal women. This medication signals the body to stop producing estrogen, depriving the tumor of the estrogen it needs to grow. Several weeks are needed before tumor growth slows. Side effects include hot flashes, sexual dysfunction, increased pain, and rash.

Aromatase inhibitors (e.g., anastozole [Arimidex®], letrozole [Femara®], exemestane [Aromasin®] inhibit the action of the enzyme aromatase, which is involved in estrogen production in postmenopausal women. These drugs may be prescribed for postmenopausal women with advanced breast cancer that has been unsuccessfully treated with tamoxifen. Side effects include the following: cough, depression, diarrhea, dizziness, fatigue, headache, hot flashes, increased appetite, nausea and pain.

Chemotherapy is a systemic treatment i.e., travels throughout the body via the bloodstream, that often uses a combination of drugs to slow tumor growth and destroy cancer cells. Drugs may be administered orally or intravenously. Chemotherapy is often used as an adjuvant therapy to destroy breast cancer cells that have metastasized to the lymph nodes. It also is used to shrink the tumor prior to surgery (neoadjuvant therapy) and as a primary treatment.

The combination most commonly prescribed to treat breast cancer is doxorubicin (Doxil®) and cyclophosphamide (Cytoxin®). Paclitaxel (Taxol®, or the generic form, Paxene®) is often prescribed after this combination treatment, when breast cancer has metastasized to the lymph nodes. It is also prescribed following breast cancer surgery. Other chemotherapy drugs include docetaxel (Taxotere®) and gemcitabine (Gemzar®).

Side effects are often severe and include fatigue, hair loss (alopecia), fever, low blood cell count (e.g., anemia, neutropenia, thrombocytopenia), infection and nausea.

Biological therapy (also called immunotherapy) involves using trastuzumab (Herceptin®) to inhibit tumor growth and enhance the immune system's ability to fight cancer. It also may be combined with chemotherapy as a first line treatment for metastatic breast cancer and may be used after chemotherapy or anti-estrogen therapy to improve the effectiveness of the treatment. When used alone or in combination, side effects include cardiac dysfunction (causes severe cough, shortness of breath, difficulty performing physical activities), chills, congestive heart failure, cough, diarrhea, fever, headache, nausea, weakness and vomiting.

Despite the positive results obtained in clinical applications in chemotherapy, the search for new compounds and compositions is still open to the identification of new compounds with optimal features of reduced toxicity and increased tumor selectivity.

SUMMARY OF THE INVENTION

The present invention is a chemical composition and a method for administration for the treatment of malignant tumors in mammals, including carcinomas, sarcomas, and lymphomas. The composition of the present invention, has been found to be particularly effective with respect to the treatment of carcinomas of the breast and lymphomas.

It is an object of the present invention to provide a chemotherapeutic composition and method for treating mammalian cancers of the breast, the lymphatic system, such as Hodgkins and non-Hodgkins lymphoma, Burkitts lymphoma, and Ehrlich's ascites tumor.

DETAILED DESCRIPTION OF THE INVENTION

It has been found that a composition comprising a mixture of ammoniated mercury, zinc oxide and citric acid when administered to a mammal suffering from a variety of cancers provides an effective method for treating such mammalian cancers.

The quantity of ammoniated mercury in the composition of the present invention can be from about 0.1 grams to about 10 grams, with the preferred quantity being 0.2 grams. The amount of zinc oxide in the composition can be from about 0.1 grams to about 50 grams, with 0.1 grams being preferred. The quantity of citric acid present in the medicinal composition of the present invention can be from about 0.1 grams to about 100 grams, with 50 grams being the preferred quantity.

The composition of the present invention is prepared, in a preferred embodiment, by adding 50 gm of citric acid to 100 ml of distilled water and heating until a temperature of 80° C. is reached. Then 0.2 gm of ammoniated mercury is added to the citric acid solution and mixed well until the ammoniated mercury is dissolved. Then 0.1 gm of zinc oxide is added with mixing until dissolution occurs. The solution containing the three (3) ingredients is then added to 900 ml of distilled water and heated to 90° C., with stirring for five (5) minutes. The solution is then allowed to cool for three hours.

The composition of the present invention can be used effectively in various forms, such as tablets, capsules, suppositories or solutions. The various forms can be prepared by known methods using conventional solid carriers, such as, for example, lactose, starch and talcum, or by using liquid carriers, such as, for example, water, fatty oils, essential oils, liquid paraffins and alcohol.

Other carriers which may be employed to advantage include animal and vegetable proteins, such as gelatins, dextrins and soy; gums such as acacia, guar, agar and xanthan; polysaccharides, alginates; carboxymethylcelluloses; carragenans, dextrans, pectins; synthetic polymers, such as polyvinylperrolidone; sugars such as mannitol, dextrose, galactose, and trehalose; inorganic salts, such as sodium phosphate, sodium chloride, and aluminum silicates, and amino acids having from 2 to 12 carbon atoms such as glycine, L-alanine, L-aspartic acid, L-glutamic acid, L-hydroxyproline, L-isoleucine, L-lucine, and L-phenylalanine.

Auxiliary components which can optionally be added during compounding include tablet disintegrants, solubilizers, preservatives, anti-oxidants, surfactants, viscosity enhancers, coloring agents, flavoring agents, pH modifiers, sweeteners and taste-making agents among others. Exemplary coloring agents, which can be used, include red, black and yellow iron oxides and FD&C dyes, including FD&C Blue No. 2 and Red No. 40. Examples of the flavoring agents which can be used to advantage are mint, raspberry, licorice, orange, lemon, grapefruit, caramel, grape and combinations thereof. Suitable pH modifiers include citric acid, tartaric acid, phosphoric acid, hydrochloric acid, and maleic acid. Suitable sweeteners include aspartame, acesulfane K and thaumatin. Taste-masking agents which can be used include sodium bicarbonate, ion-exchange resins, cyclodextrin inclusion compounds, adsorbates, and microencapsulated actives.

The composition of the present invention can be administered in a variety of modes. For example, the administration may be oral, parenteral, including subcutaneous, e.g., by injection or by depot tablet, intradermal, intrathecal, intramuscular, e.g., by depot, intravenously, rectal, or topical, including dermalbuccal and sublingual. Formulations for oral administration may be presented as discrete units, such as capsules, cachets, or tablets, each containing a predetermined amount of the active ingredients; as a powder or granules, as a solution or in suspension in an aqueous liquid or a non-aqueous liquid; or as an oil-in-water liquid.

Formulations for parenteral administration include aqueous and non-aqueous sterile injection solutions, which may contain anti-oxidants, buffers, bacteriostats and solvents which render the composition isotonic with the blood of the intended recipient, as well as aqueous and non-aqueous sterile suspensions which may include suspending agents and thickening agents.

Oral administration in the form of a liquid solution is the preferred method for the administration of the composition of the present invention. The dosage level is dependent upon a number of factors, including the weight and physical condition of the patient, the particular condition which is being treated, and the amount of the active ingredients present in the administered dose. For example, a suitable dose for an 160 lb. adult male is from about 1 to about 5 mls., either 3 or 4 times daily.

The composition of the present invention has been found to result in the normalization of certain physiological parameters, namely, organ weight and level of erythrocytes and leucocytes, extension of the latent period and reduction of tumor weights.

EXAMPLE 1

The antitumor activity of the medication of the present invention was studied in mice and rats with transplantable tumors of Sarcoma 37, 45, and 180, and Ehrlich ascites tumor.

Necrosis-free pieces of tumoral tissue (a peripheral part of a tumoral node) cut with scissors to form a homogeneous mass served as transplantants for solid models (Sarcomas 37, 45 and 180). A sterile physiological solution in the proportion of 1:3-1:4 was added to the tumor and the resulting suspension was introduced with a syringe subcutaneously to the animals. The transplantation was conducted in sterile box conditions using 12-14 days' tumor as a donor. The transplantation of sarcomas 37 and 180 was performed by means of subcutaneous introduction of 0.2-0.3 ml of the 20% tumoral suspension in a physiological solution to the axillary crease of each mouse. For the transplantation of Sarcoma 45, by 0.4-0.5 ml of suspension of tumoral cells was introduced subcutaneously (to the lateral area) of each rat. On the $4^{th}$-$5^{th}$ days after inoculation, when the transplanted tumor is usually pea-size, the animals were divided into test and control groups each having 8 mice and 10 rats. Within 6-8 days, the medicated composition of the present invention was introduced to the animals in the test groups through a gastric tube. A day after the last injection of the medication, the animals were killed with ether, weighed, and the weight of tumors was measured separately. The therapeutic effect was estimated by the percent of tumor growth suppression (TGS) compared to the control group.

As a reference medication for comparative assessment of the therapeutic action of the present invention under analogous experimental conditions, 5-fluorouracil was used, an antimetabolite largely applied in oncological practice, considering that by the mechanism of antitumoral action phytogenic medications are more similar to antimetabolites than to alkylating agents.

In the case of Ehrlich ascites tumor, the tumor was transplanted to mice intraperitoneally. Under sterile conditions, the ascitic fluid was taken from animals with 8-10 days' ascetic tumor and introduced into the abdominal cavity of healthy mice by 0.2 ml. Twenty-four (24) hours after the transplantation, the animals were divided into groups and start to receive the medication once a day within 6 days. After introduction of the medication ceased, the animals were killed and weighed. The ascetic fluid was extracted from the abdominal cavity. Then the mice were weighed again to estimate the volume of ascetic fluid. The therapeutic effectiveness was estimated on the basis of the obtained weight data.

In the study of antitimor properties of the medication of the present invention, the medication was used in doses of 20 and 40 ml/kg, and 10 and 30 ml/kg in the tests on mice and rats, respectively. The general toxic action which the medication had on the organism of the tested animals was estimated by their outer appearance and behavior during the experiment, as well as by the Growth Ratio ($G_R$) expressed in percent.

The numerical data obtained was processed statistically by Student-Fisher's method. The data were considered reliable in case of $P<0.05$.

The results of the chemotherapeutic experiments summarized in the table below attest that the medication or composition of the present invention displays notable antitumor activity with respect to the Ehrlich ascites tumor. In doses of 20 and 40 ml/kg, the medication causes inhibition of ascit accumulation by 52% ($P<0.05$) and 56% ($P<0.05$), respectively. Under analogous experimental conditions, the antitumor effect of 5-fluorouracil reference medication used in the optimal therapeutic dose of 25 ml/kg comprised 70% ($P<0.05$). The data presented in Table 1 leads to the conclusion that the preparation is less effective with respect to the sarcoma models.

The medication caused a slight inhibition of the growth of the mentioned tumors only when applied in relatively high concentrations (30 ml/kg for rats and 40 ml/kg for mice). The therapeutic action of the preparation in the tests with Sarcomas 45, 37 and 180 comprised, respectively, 32, 36 and 34% ($P=0.05$). In lower concentrations, the antitumor activity of the medication for the listed models did not exceed 24% ($P>0.05$).

Under identical experimental conditions, 5-fluorouracil synthetic antitumoral medication inhibited the growth of Sarcomas 45 and 180 by 32% ($P=0.05$) and 45% ($P<0.05$), respectively. Its therapeutic effect equaled 70% only in the tests with Sarcoma 37 ($P<0.05$).

It is important to note that systematic observation of animals along with the course of introduction of the composition of the present invention in all chemotherapeutic experiments did not reveal any changes of their general condition, or behavior. In all cases, the animals' growth rate indicators for the medication had positive values and varied from 5.4 to 8.0% (Table 1), which indicates a large increase in weight, or a lower weight loss of the treated animals in the course of the experiment, and provides indirect evidence of lack of toxic action of the medication on the animals' organism. Under similar experimental conditions, the $G_R$ for 5-fluorouracil had negative values (from −7.3 to −11) in all tests, which indicates clear toxic action of the medication on the organism of the test animals.

TABLE 1

| Tumors | Dose (ml/kg) | TGS, % | $G_R$ % |
| --- | --- | --- | --- |
| Ehrlich Ascites Tumor | 20 | 52 (P < 0.05) | 7.6 |
| | 40 | 56 (P < 0.05) | 6.3 |
| Sarcoma 180 | 20 | 21 (<0.05) | 6.4 |
| | 40 | 34 (P = 0.05) | 6.1 |
| Sarcoma 37 | 20 | 24 (P > 0.05) | 5.4 |
| | 40 | 36 (P = 0.05) | 6.7 |
| Sarcoma 45 | 10 | 22 (P > 0.05) | 8.0 |
| | 30 | 32 (P = 0.05) | 7.6 |

Therefore, the data show that the invention displays an antitumor activity with respect to some of transplantable animal tumors.

The antitumor activity of the composition of the present invention attests that this medication has a therapeutic action with respect to the Ehrlich ascites tumor. High concentrations of the composition cause inhibition of growth of the sarcomas without having any toxic action on the organism of tested animals.

While the illustrative embodiments of the invention have been described with particularity, it will be understood that numerous modifications will be apparent to, and can readily be made, by those of ordinary skill in the art. Accordingly, it is not intended that the scope of the claims appended hereto be limited to the example and descriptions set forth herein, but rather, that the claims be construed as encompassing all the features of patentable novelty which reside in the present invention, including all features which would be treated as equivalents thereof by those of ordinary skill in the art to which this invention pertains.

What is claimed is:

1. An anti-tumor composition a comprising about 0.1 to about 10 grams of ammoniated mercury, about 0.1 to about 50 grams of zinc oxide and about 0.1 to about 100 grams of citric acid.

2. The anti-tumor composition of claim 1, wherein the composition is in the form of a solution, suspension, tablet, capsule or suppository.

3. The anti-tumor composition of claim 2, wherein the composition is a solution in dosage form, each dose including from about 1 ml to about 5 ml of the composition.

* * * * *

UNITED STATES PATENT AND TRADEMARK OFFICE
CERTIFICATE OF CORRECTION

| | | |
|---|---|---|
| PATENT NO. | : 8,007,832 B2 | Page 1 of 1 |
| APPLICATION NO. | : 11/504850 | |
| DATED | : August 30, 2011 | |
| INVENTOR(S) | : Babikian et al. | |

It is certified that error appears in the above-identified patent and that said Letters Patent is hereby corrected as shown below:

Title Page, Insert:

-- Related U.S. Application Data

(60) Provisional application No. 60/710,820, filed on August 23, 2005. --.

Signed and Sealed this
Twenty-seventh Day of December, 2011

David J. Kappos
*Director of the United States Patent and Trademark Office*